United States Patent
Gupta et al.

(10) Patent No.: US 10,692,014 B2
(45) Date of Patent: *Jun. 23, 2020

(54) ACTIVE USER MESSAGE DIET

(71) Applicant: Microsoft Technology Licensing, LLC, Redmond, WA (US)

(72) Inventors: Rupesh Gupta, Sunnyvale, CA (US); Guanfeng Liang, Fremont, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 448 days.

This patent is subject to a terminal disclaimer.

(21) Appl. No.: 15/194,300

(22) Filed: Jun. 27, 2016

(65) Prior Publication Data

US 2017/0372038 A1    Dec. 28, 2017

(51) Int. Cl.

| | |
|---|---|
| G06Q 30/02 | (2012.01) |
| G06Q 10/10 | (2012.01) |
| G06Q 10/06 | (2012.01) |
| G06Q 40/02 | (2012.01) |
| G06Q 99/00 | (2006.01) |
| G06N 20/00 | (2019.01) |
| G06Q 50/00 | (2012.01) |
| G16H 40/63 | (2018.01) |

(Continued)

(52) U.S. Cl.
CPC ............ *G06N 20/00* (2019.01); *G06Q 50/01* (2013.01); *G16H 10/60* (2018.01); *G16H 20/60* (2018.01); *G16H 40/63* (2018.01); *G16H 50/20* (2018.01); *G16H 50/50* (2018.01); *G06N 3/08* (2013.01); *G06N 5/003* (2013.01); *G06N 7/005* (2013.01); *G06N 20/10* (2019.01)

(58) Field of Classification Search
CPC .... G06Q 50/01; G06F 19/3475; G06N 7/005; G06N 9/005; G06N 20/00; G06N 5/003; G06N 3/08; G06N 20/10; G16H 40/63; G16H 10/60; G16H 50/50; G16H 20/60; G16H 50/20
USPC .................................................. 705/1.1–912
See application file for complete search history.

(56) References Cited

U.S. PATENT DOCUMENTS 7,143,091 B2 * 11/2006 Charnock ......... G06F 17/30716
8,571,930 B1 * 10/2013 Galperin ............ G06Q 30/0273
705/14.43

(Continued)

*Primary Examiner* — Jonathan P Ouellette
(74) *Attorney, Agent, or Firm* — Schwegman Lundberg & Woessner, P.A.

(57) ABSTRACT

A system, a machine-readable storage medium storing instructions, and a computer-implemented method are described herein are directed to a Message Diet Engine that generates a pool of messages for a plurality member accounts of a social network service. Each message being of a respective message type from a plurality of message types and targeted to a specific member account. For each respective member account, the Message Diet Engine selects a minimum number of messages, from the pool of messages, targeted to the respective member account that prompts an expected social network activity target and avoids an expected number of complaints. Based on the selected minimum number of messages for each respective member account, the Message Diet Engine identifies a total minimum number of messages, from the pool of messages, to be sent to the plurality of member accounts that prompts an expected total social network activity target and avoids a total expected number of complaints.

20 Claims, 7 Drawing Sheets

(51) Int. Cl.
  *G16H 10/60* (2018.01)
  *G16H 50/50* (2018.01)
  *G16H 50/20* (2018.01)
  *G16H 20/60* (2018.01)
  *G06N 7/00* (2006.01)
  *G06N 5/00* (2006.01)
  *G06N 3/08* (2006.01)
  *G06N 20/10* (2019.01)

(56) References Cited

U.S. PATENT DOCUMENTS

| | | | | |
|---|---|---|---|---|
| 2011/0060649 A1* | 3/2011 | Dunk | ............... | G06F 17/3002 705/14.53 |
| 2011/0313842 A1* | 12/2011 | Avner | ............... | G06Q 30/0241 705/14.41 |
| 2012/0272160 A1* | 10/2012 | Spivack | ............... | G06Q 10/10 715/752 |
| 2013/0018964 A1* | 1/2013 | Osipkov | ............... | G06Q 10/107 709/206 |
| 2013/0097019 A1* | 4/2013 | Ferber | ............... | G06Q 30/02 705/14.53 |
| 2013/0291105 A1* | 10/2013 | Yan | ............... | G06Q 10/06 726/22 |
| 2014/0229407 A1* | 8/2014 | White | ............... | G06N 99/005 706/12 |
| 2014/0229487 A1* | 8/2014 | Mukund | ............... | G06F 17/30035 707/740 |
| 2015/0347924 A1* | 12/2015 | Zeng | ............... | H04L 51/30 706/12 |
| 2016/0071162 A1* | 3/2016 | Ogawa | ............... | G06Q 30/0269 705/14.66 |
| 2016/0239918 A1* | 8/2016 | Lambur | ............... | G06Q 40/06 |

* cited by examiner

US 10,692,014 B2

ACTIVE USER MESSAGE DIET

TECHNICAL FIELD

The present disclosure generally relates to data processing systems. More specifically, the present disclosure relates to methods, systems and computer program products for identifying a set of messages to be sent to a plurality of member accounts of a social networking service.

BACKGROUND

A social networking service is a computer- or web-based application that enables users to establish links or connections with persons for the purpose of sharing information with one another. Some social networking services aim to enable friends and family to communicate with one another, while others are specifically directed to business users with a goal of enabling the sharing of business information. For purposes of the present disclosure, the terms "social network" and "social networking service" are used in a broad sense and are meant to encompass services aimed at connecting friends and family (often referred to simply as "social networks"), as well as services that are specifically directed to enabling business people to connect and share business information (also commonly referred to as "social networks" but sometimes referred to as "business networks").

With many social networking services, members are prompted to provide a variety of personal information, which may be displayed in a member's personal web page. Such information is commonly referred to as personal profile information, or simply "profile information", and when shown collectively, it is commonly referred to as a member's profile. For example, with some of the many social networking services in use today, the personal information that is commonly requested and displayed includes a member's age, gender, interests, contact information, home town, address, the name of the member's spouse and/or family members, and so forth. With certain social networking services, such as some business networking services, a member's personal information may include information commonly included in a professional resume or curriculum vitae, such as information about a person's education, employment history, skills, professional organizations, and so on. With some social networking services, a member's profile may be viewable to the public by default, or alternatively, the member may specify that only some portion of the profile is to be public by default. Accordingly, many social networking services serve as a sort of directory of people to be searched and browsed.

DESCRIPTION OF THE DRAWINGS

Some embodiments are illustrated by way of example and not limitation in the figures of the accompanying drawings in which.

DETAILED DESCRIPTION

Figure 1:
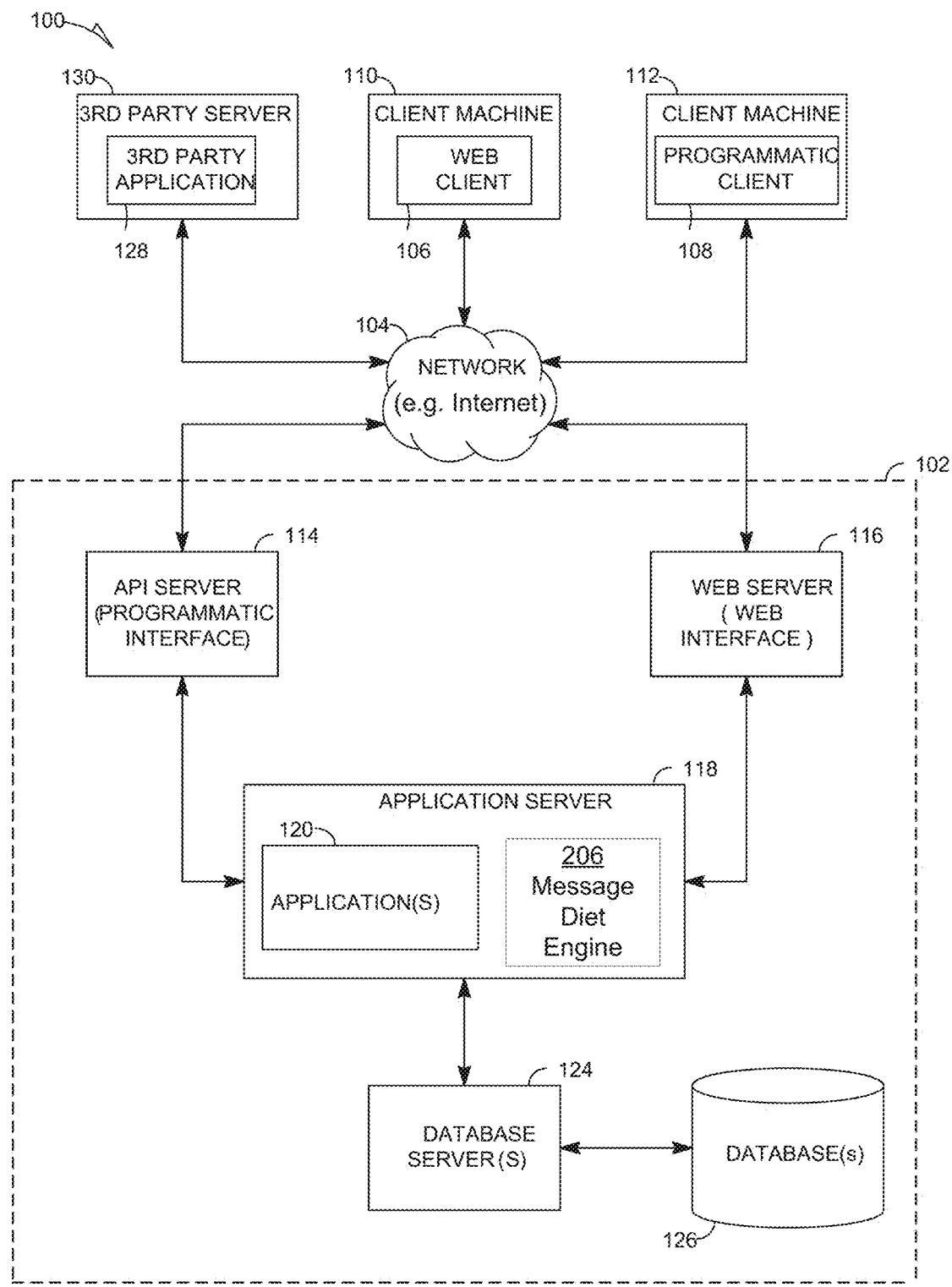
FIG. 1 is a block diagram illustrating a client-server system, in accordance with an example embodiment.

The present disclosure describes methods and systems for identifying a total minimum number messages to be sent to a plurality of member accounts that meets multiple constraints. In the following description, for purposes of explanation, numerous specific details are set forth in order to provide a thorough understanding of the various aspects of different embodiments of the present invention. It will be evident, however, to one skilled in the art, that the present invention may be practiced without all of the specific details.

A system, a machine-readable storage medium storing instructions, and a computer-implemented method are described herein are directed to a Message Diet Engine that generates a pool of messages for a plurality member accounts of a social network service. Each message being of a respective message type from a plurality of message types and targeted to a specific member account. For each respective member account, the Message Diet Engine selects a minimum number of messages, from the pool of messages, targeted to the respective member account that prompts an expected social network activity target and avoids an expected number of complaints. Based on the selected minimum number of messages for each respective member account, the Message Diet Engine identifies a total minimum number of messages, from the pool of messages, to be sent to the plurality of member accounts that prompts an expected total social network activity target and avoids a total expected number of complaints.

According to various exemplary embodiments, the Message Diet Engine determines a minimum number of total messages sent to a plurality of member accounts such that the total minimum number of sent messages prompts a desired level of member account activity while avoiding receipt of a threshold number of complaints. The Message Diet Engine selects the messages from a pool of messages, where each message is already targeted for a particular member account from the plurality of member accounts. As such, each message in the pool of messages is inherently targeted for a member account to the exclusion of the other member accounts.

The Message Diet Engine collects historical data related to previous messages sent to various member accounts and the corresponding responses to each respective previous message. A response can be, for example, an increase in member account activity due to message receipt or a member account complaint due to message receipt. The Message Diet Engine builds and trains machine learning models (or regression models) based on the historical data. The Message Diet Engine builds an Expected Activity model and an Expected Complaints model. The Expected Activity model learns regression coefficients (hereinafter "w") that represent how likely a type of message will prompt member account activity for a member account having a particular set of features or attributes. For example, a first w coefficient represents a likelihood that a first type of message sent to a member account having a first set of features will prompt increased engagement. A second w coefficient represents a likelihood that same first type of message sent to a member account having a second set of features will prompt increased engagement. A third w coefficient represents a likelihood that a second type of message sent to the member account having the first set of features will prompt the member account to become more active. A fourth w coefficient represents a likelihood that the same second type of message sent to the member account having the second set of features will prompt the member account to become more active. Therefore, each w regression coefficient of the Expected Activity model is based on a particular message type and a particular set of features or attributes of a given member account. There can be different versions of a w regression coefficient for each particular message type with respect to various sets of member account features. The Expected Activity model returns, for each member account, an expected probability output between 0-1 that represents how likely that member account will be active if a given set of messages (specifically targeted to the member account) is selected from the pool of messages and sent to the member account. It is understood that a feature, as used herein, is data, attribute(s) and/or a profile characteristic, of a given member account that has been learned by the Message Diet Engine 206 as being predictive of whether the given member account will perform an action with regard to a particular type of content, such as a message.

The Expected Complaints model learns regression coefficients (hereinafter "c") that represent how likely a particular type of message will prompt a member account having a particular set of features or attributes to respond with complaint activity. For example, a first c coefficient represents a likelihood that the first type of message sent to a member account having the first set of features will prompt complaint activity by the member account. A second c coefficient represents a likelihood that the same first type of message sent to the member account having the second set of features will prompt complaint activity by the member account. A third c coefficient represents a likelihood that the second type of message sent to the member account having the first set of features will prompt complaint activity by the member account. A fourth c coefficient represents a likelihood that the same second type of message sent to the member account having the second set of features will prompt complaint activity by the member account. Therefore, similar to the Expected Activity model, each c regression coefficient of the Expected Activity model is based on a particular type of message and a particular set of features or attributes of a given member account. There can be different versions of a c regression coefficient for each particular message type with respect to various sets of member account features. The Expected Complaints model returns, for each member account, an expected number of complaints that may be received if a given set of messages (specifically targeted to the member account) is selected from the pool of messages and sent to the member account.

The Message Diet Engine builds and trains the Expected Activity model and the Expected Complaints model for the purpose of solving a multi-objective optimization problem. That is, the Message Diet Engine returns a total minimum number of messages to be sent to all of the plurality of member accounts that ensures a target expected level of overall member account activity, while not exceeding a threshold number of expected complaints received from the plurality of member accounts. However, the number of each type of messages in a set of messages to be sent to each respective member account is not initially known. Each amount of message types to be included in each set of messages to be sent to a respective member account has to be identified in order to determine whether the target expected level of overall member account activity can be met and whether the threshold number of expected complaints can be avoided.

As described in various embodiments, the Message Diet Engine may be a configuration-driven system for building, training, and deploying logistic regression models. In particular, the operation of the Message Diet Engine is completely configurable and customizable by a user through a user-supplied configuration file such as a JavaScript Object Notation (JSON), eXtensible Markup Language (XML) file, etc. For example, each module in the Message Diet Engine may have text associated with it in the configuration file that describes how the module is configured, the inputs to the module, the operations to be performed by the module on the inputs, the outputs from the module, and so on. Accordingly, the user may rearrange the way these modules are connected together as well as the rules that the various modules use to perform various operations. Thus, whereas conventional modeling is often performed in a fairly ad hoc and code driven manner, the modules of the Message Diet Engine may be configured in a modular and reusable fashion, to enable more efficient prediction modeling.

As understood by those skilled in the art, logistic regression is an example of a statistics-based machine learning technique that uses a logistic function. The logistic function is based on a variable, referred to as a logit. The logit is defined in terms of a set of regression coefficients of corresponding independent predictor variables. Logistic regression can be used to predict the probability of occurrence of an event given a set of independent/predictor variables.

The independent/predictor variables of the logistic regression model are the attributes represented by the assembled feature vectors described throughout. The regression coefficients may be estimated using maximum likelihood or learned through a supervised learning technique from data collected in logs or calculated from log data, as described in more detail below. Accordingly, once the appropriate regression coefficients are determined, the features included in the assembled feature vector may be plugged in to the logistic regression model in order to predict the probability that the event Y occurs (where the event Y may be, for example, whether the particular member account becomes more active). In other words, provided an assembled feature vector including various features associated with a particular member, the assembled feature vector may be applied to a logistic regression model to determine the probability that the particular member will respond to the particular content item in a particular way (e.g., click) given the particular context. Logistic regression is well understood by those skilled in the art, and will not be described in further detail herein, in order to avoid occluding various aspects of this disclosure.

The Message Diet Engine may use various other prediction modeling techniques understood by those skilled in the art to predict whether a particular member will click on a particular content item in a particular context. For example, other prediction modeling techniques may include other machine learning models such as a Naïve Bayes model, a support vector machines (SVM) model, a decision trees model, and a neural network model, all of which are understood by those skilled in the art.

According to various exemplary embodiments, the Message Diet Engine and associated user-supplied configuration file may be used for the purposes of both off-line training (for generating, training, and refining one or more machine learning models) and online inferences (for predicting expected member account activity and complaints).

It is understood that various embodiments further include encoded instructions that comprise operations to generate a user interface(s) and various user interface elements. The user interface and the various user interface elements can be displayed to be representative of any of the operations, models, expected activity, expected complaints and a set(s) of messages to be sent, as described herein. In addition, the user interface and various user interface elements are generated by the Message Diet Engine for display on a computing device, a server computing device, a mobile computing device, etc.

Turning now to FIG. 1, FIG. 1 is a block diagram illustrating a client-server system, in accordance with an example embodiment. A networked system 102 provides server-side functionality via a network 104 (e.g., the Internet or Wide Area Network (WAN)) to one or more clients. FIG. 1 illustrates, for example, a web client 106 (e.g., a browser) and a programmatic client 108 executing on respective client machines 110 and 112.

An Application Program Interface (API) server 114 and a web server 116 are coupled to, and provide programmatic and web interfaces respectively to, one or more application servers 118. The application servers 118 host one or more applications 120. The application servers 118 are, in turn, shown to be coupled to one or more database servers 124 that facilitate access to one or more databases 126. While the applications 120 are shown in FIG. 1 to form part of the networked system 102, it will be appreciated that, in alternative embodiments, the applications 120 may form part of a service that is separate and distinct from the networked system 102.

Further, while the system 100 shown in FIG. 1 employs a client-server architecture, the present disclosure is of course not limited to such an architecture, and could equally well find application in a distributed, or peer-to-peer, architecture system, for example. The various applications 120 could also be implemented as standalone software programs, which do not necessarily have networking capabilities.

The web client 106 accesses the various applications 120 via the web interface supported by the web server 116. Similarly, the programmatic client 108 accesses the various services and functions provided by the applications 120 via the programmatic interface provided by the API server 114.

FIG. 1 also illustrates a third party application 128, executing on a third party server machine 130, as having programmatic access to the networked system 102 via the programmatic interface provided by the API server 114. For example, the third party application 128 may, utilizing information retrieved from the networked system 102, support one or more features or functions on a website hosted by the third party. The third party website may, for example, provide one or more functions that are supported by the relevant applications of the networked system 102. In some embodiments, the networked system 102 may comprise functional components of a professional social network.

Figure 2:
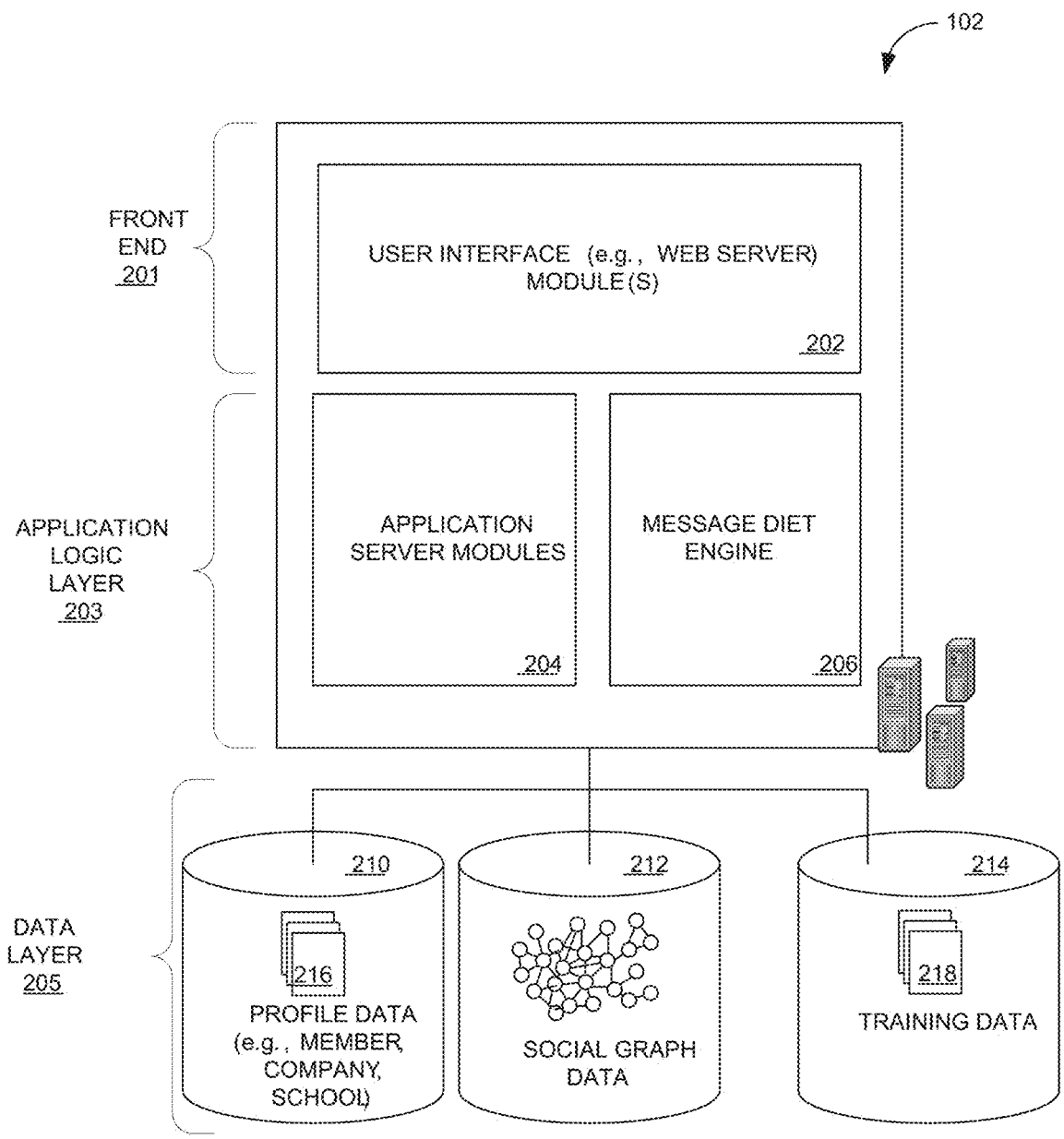
FIG. 2 is a block diagram showing functional components of a professional social network within a networked system, in accordance with an example embodiment.

FIG. 2 is a block diagram showing functional components of a professional social network within the networked system 102, in accordance with an example embodiment.

As shown in FIG. 2, the professional social network may be based on a three-tiered architecture, consisting of a front-end layer 201, an application logic layer 203, and a data layer 205. In some embodiments, the modules, systems, and/or engines shown in FIG. 2 represent a set of executable software instructions and the corresponding hardware (e.g., memory and processor) for executing the instructions. To avoid obscuring the inventive subject matter with unnecessary detail, various functional modules and engines that are not germane to conveying an understanding of the inventive subject matter have been omitted from FIG. 2. However, one skilled in the art will readily recognize that various additional functional modules and engines may be used with a professional social network, such as that illustrated in FIG. 2, to facilitate additional functionality that is not specifically described herein. Furthermore, the various functional modules and engines depicted in FIG. 2 may reside on a single server computer, or may be distributed across several server computers in various arrangements. Moreover, although a professional social network is depicted in FIG. 2 as a three-tiered architecture, the inventive subject matter is by no means limited to such architecture. It is contemplated that other types of architecture are within the scope of the present disclosure.

As shown in FIG. 2, in some embodiments, the front-end layer 201 comprises a user interface module (e.g., a web server) 202, which receives requests and inputs from various client-computing devices, and communicates appropriate responses to the requesting client devices. For example, the user interface module(s) 202 may receive requests in the form of Hypertext Transport Protocol (HTTP) requests, or other web-based, application programming interface (API) requests.

In some embodiments, the application logic layer 203 includes various application server modules 204, which, in conjunction with the user interface module(s) 202, generates various user interfaces (e.g., web pages) with data retrieved from various data sources in the data layer 205. In some embodiments, individual application server modules 204 are used to implement the functionality associated with various services and features of the professional social network. For instance, the ability of an organization to establish a presence in a social graph of the social network service, including the ability to establish a customized web page on behalf of an organization, and to publish messages or status updates on behalf of an organization, may be services implemented in independent application server modules 204. Similarly, a variety of other applications or services that are made available to members of the social network service may be embodied in their own application server modules 204.

As shown in FIG. 2, the data layer 205 may include several databases, such as a database 210 for storing profile data 216, including both member profile attribute data as well as profile attribute data for various organizations. Consistent with some embodiments, when a person initially registers to become a member of the professional social network, the person will be prompted to provide some profile attribute data such as, such as his or her name, age (e.g., birthdate), gender, interests, contact information, home town, address, the names of the member's spouse and/or family members, educational background (e.g., schools, majors, matriculation and/or graduation dates, etc.), employment history, skills, professional organizations, and so on. This information may be stored, for example, in the database 210. Similarly, when a representative of an organization initially registers the organization with the professional social network the representative may be prompted to provide certain information about the organization. This information may be stored, for example, in the database 210, or another database (not shown). With some embodiments, the profile data 216 may be processed (e.g., in the background or offline) to generate various derived profile data. For example, if a member has provided information about various job titles the member has held with the same company or different companies, and for how long, this information can be used to infer or derive a member profile attribute indicating the member's overall seniority level, or a seniority level within a particular company. With some embodiments, importing or otherwise accessing data from one or more externally hosted data sources may enhance profile data 216 for both members and organizations. For instance, with companies in particular, financial data may be imported from one or more external data sources, and made part of a company's profile.

The profile data 216 may also include information regarding settings for members of the professional social network. These settings may comprise various categories, including, but not limited to, privacy and communications. Each category may have its own set of settings that a member may control.

Once registered, a member may invite other members, or be invited by other members, to connect via the professional social network. A "connection" may require a bi-lateral agreement by the members, such that both members acknowledge the establishment of the connection. Similarly, with some embodiments, a member may elect to "follow" another member. In contrast to establishing a connection, the concept of "following" another member typically is a unilateral operation, and at least with some embodiments, does not require acknowledgement or approval by the member that is being followed. When one member follows another, the member who is following may receive status updates or other messages published by the member being followed, or relating to various activities undertaken by the member being followed. Similarly, when a member follows an organization, the member becomes eligible to receive messages or status updates published on behalf of the organization. For instance, messages or status updates published on behalf of an organization that a member is following will appear in the member's personalized data feed or content stream. In any case, the various associations and relationships that the members establish with other members, or with other entities and objects, may be stored and maintained as social graph data within a social graph database 212.

The professional social network may provide a broad range of other applications and services that allow members the opportunity to share and receive information, often customized to the interests of the member. For example, with some embodiments, the professional social network may include a photo sharing application that allows members to upload and share photos with other members. With some embodiments, members may be able to self-organize into groups, or interest groups, organized around a subject matter or topic of interest. With some embodiments, the professional social network may host various job listings providing details of job openings with various organizations.

In some embodiments, the professional social network provides an application programming interface (API) module via which third-party applications can access various services and data provided by the professional social network. For example, using an API, a third-party application may provide a user interface and logic that enables an authorized representative of an organization to publish messages from a third-party application to a content hosting platform of the professional social network that facilitates presentation of activity or content streams maintained and presented by the professional social network. Such third-party applications may be browser-based applications, or may be operating system-specific. In particular, some third-party applications may reside and execute on one or more mobile devices (e.g., a smartphone, or tablet computing devices) having a mobile operating system.

The data layer 205 further includes a training data database 214 with training data 218 based on historical message data. The data layer 205 may be accessed, used, and adjusted by the Message Diet Engine 206 as will be described in more detail below in conjunction with FIGS. 3-7. Although the Message Diet Engine 206 is referred to herein as being used in the context of a professional social network, it is contemplated that it may also be employed in the context of any website or online services, including, but not limited to, content sharing sites (e.g., photo- or video-sharing sites) and any other online services that allow users to have a profile and present themselves or content to other users. Additionally, although aspects of the present disclosure are referred to herein as being used or presented in the context of a web page, it is contemplated that any user interface view (e.g., a user interface on a mobile device or on desktop software) is within the scope of the present disclosure.

Figure 3:
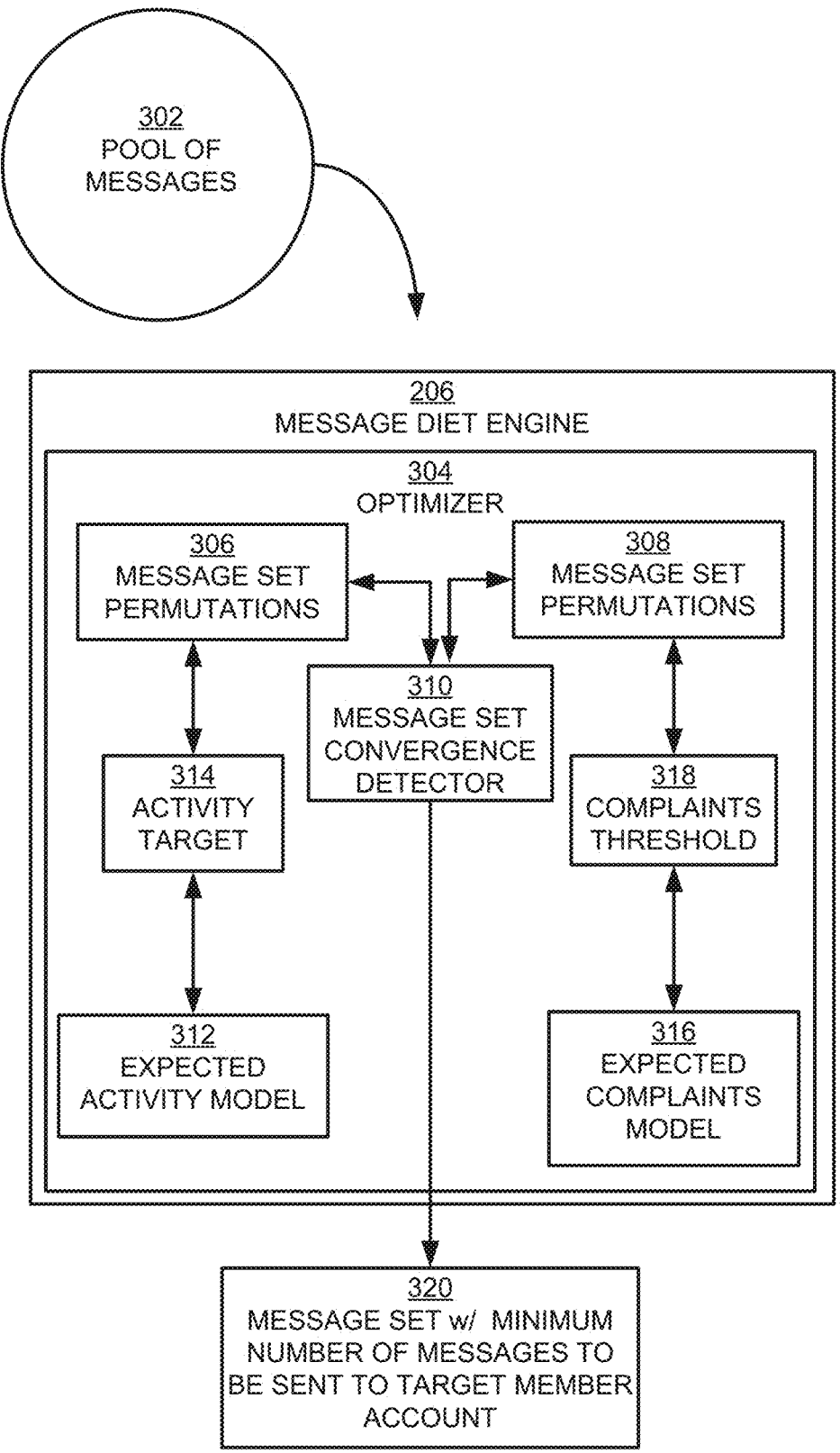
FIG. 3 illustrates a schematic diagram of an exemplary data flow in a Message Diet Engine, according to various embodiments.

FIG. 3 illustrates a schematic diagram of an exemplary data flow in a Message Diet Engine 206, according to various embodiments.

The Message Diet Engine 206 implements an Optimizer module 304 to determine each set of messages, from a pool of messages 302, to be sent to each respective member account. Using regression coefficients learned for the Expected Activity model 312 and the Expected Complaints model 316, the Optimizer module 304 continually cycles through various permutations of sets of messages 306, 308 to be sent to each respective member account. For each message set permutation, the Expected Activity model 312 returns a probability output between 0-1 indicating how likely a message set permutation will prompt the respective member account to become active and the Expected Complaints model 316 returns a number of expected complaints that will be received from a different message set permutation. It is understood that the Message Diet Engine 206 compares the probability output of the Expected Activity model 312 to the activity target 314 and the number of expected complaints returned from the Expected Complaints model 316. To the complaints threshold 318.

It is understood that each set of message permutations has various different number of type of messages. For example, a first message set permutation has 3 messages of a first message type, 2 messages of a second message type and 1 message of a third message type. A second message set permutation has 2 messages of the first message type, 2 messages of the second message type and 1 message of the third message type. A third message set permutation has 2 messages of the first message type, 3 messages of the second message type and 3 messages of the third message type. It is understood that the embodiments herein are not limited to only three message types.

As the Optimizer module 304 inputs various message set permutations 306, 308 into both the Expected Activity model 312 and the Expected Complaints model 316, a convergence detector 310 detects when the sets of messages identified by the Expected Activity model 312 and Expected Complaints 314 model converge to a select set of messages 316 that both prompts a desired level of member account activity while staying below the expected complaints threshold. The select set of messages 316 is thereby identified as a message set with a minimum number of messages, of various message types, that will meet the constraints (activity target 314, complaints threshold 318). It is understood that the activity target 314 represents an expected social network activity target and the complaints threshold 318 represents an expected number of complaints. It is understood that there can be multiple message set permutations, for a given member account, which meet the constraints of the activity target 314 and the complaints threshold 318. In the case of identifying multiple select message set permutations that meet the constraints, the Message Diet Engine 206 selects a select message set with the minimum number of messages.

The Optimizer module 304 computes a total minimum number of messages to be sent to all of the plurality of member accounts that meets or exceeds the target expected level of member account activity while staying at or below the threshold number of expected complaints. The set of messages permutation with the minimum number of messages is selected by the Optimizer module 304. In some embodiments, it is understood that that the Optimizer module 304 executes a Simplex algorithm.

Figure 4:
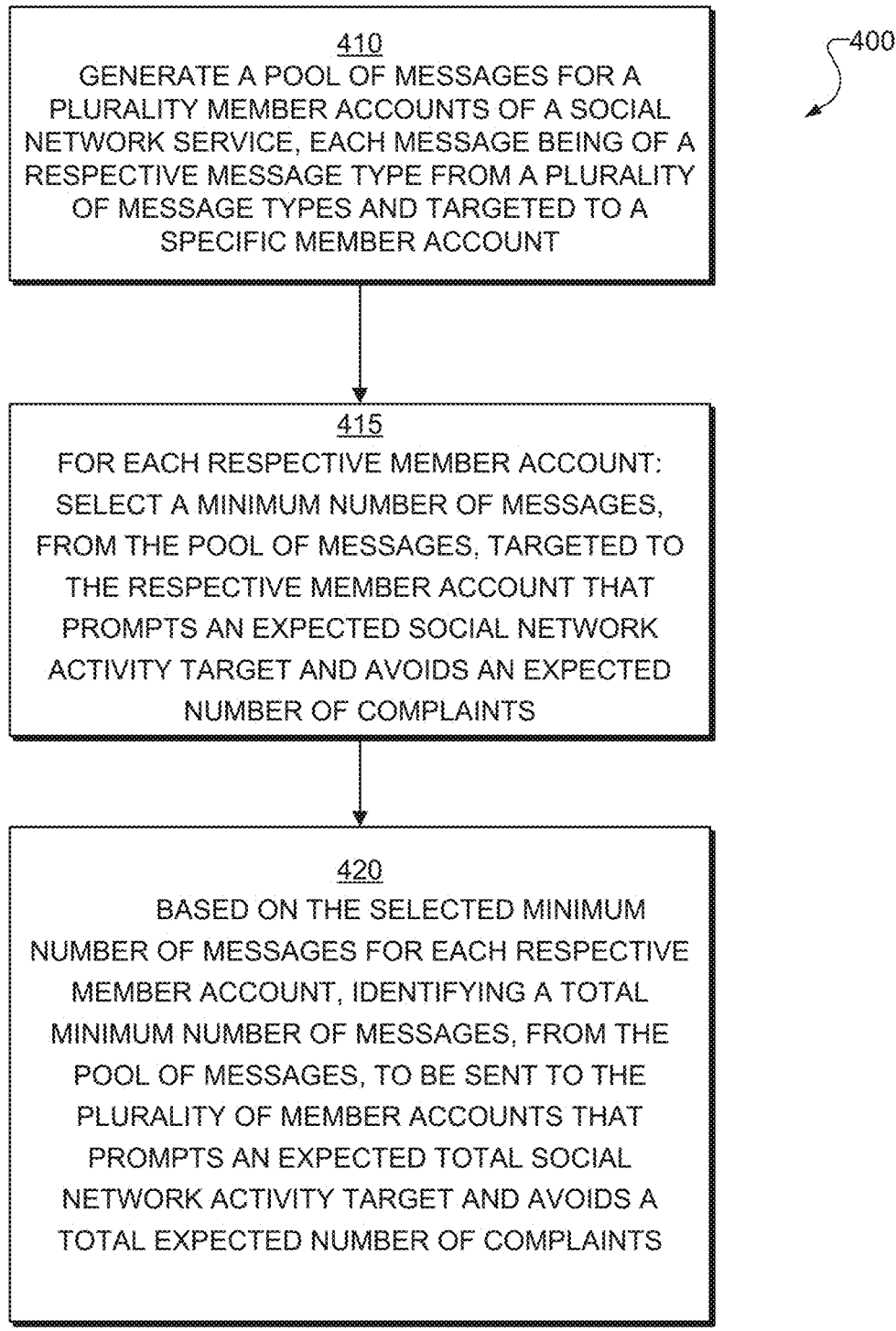
FIG. 4 is a flowchart illustrating an example method, according to various embodiments.

FIG. 4 is a flowchart 400 illustrating an example method, according to various embodiments.

At operation 410, the Message Diet Engine 206 generates a pool of messages for a plurality member accounts of a social network service, each message being of a respective message type from a plurality of message types and targeted to a specific member account. For example, the pool of message 302 includes a first plurality of messages for a first member account, a second plurality of messages for a second member account and a third plurality of messages for a third member account. The first, second and third plurality of message each include various amounts of messages of different message types.

At operation 415, for each respective member account, the Message Diet Engine 206 selects a minimum number of messages, from the pool of messages, targeted to the respective member account that prompts an expected social network activity target and avoids an expected number of complaints. For example, the Message Diet Engine 206 selects various permutations of sets of messages from the first plurality of messages targeted to the first member account. The Message Diet Engine 206 inputs various message set permutations into the expected activity model 312 and the expected complaints model 316. The expected activity model 312 provides an output indicating how much social network activity of the first member account will result from sending a given message set permutation to the first member account. The expected complaints model 316 provides an output indicating how many complaints will be received from the first member account as a result from sending a different message set permutation to the first member account.

As the various message set permutations are input into the expected activity model 312 and the expected complaints model 316, the various outputs are compared to an activity target 312 and a complaints threshold 318. The Message Diet Engine 206 monitors the output of the expected activity model 312 and the expected complaints model 316 with respect to the activity target 312 and a complaints threshold 318 in order to identify a message set permutation that both meets or exceeds the activity target 312 and falls below the complaints threshold 318. The Message Diet Engine 206 identifies a select message set permutation to be sent to the first member account.

The select message set permutation includes a total minimum number messages that, when sent to the first member account, both meets or exceeds the activity target 312 and falls below the complaints threshold 318. The select message set permutation include various amounts of message of different types. It is understood that the Message Diet Engine 206 performs similar operations with respect to message set permutations for the second member account and the third member account to identify respective select message set permutations to be sent to the second member account and the third member account. The embodiments described herein are not limited to a first, second and third member account.

At operation 420, based on the selected minimum number of messages for each respective member account, the Message Diet Engine 206 identifies a total minimum number of messages, from the pool of messages, to be sent to the plurality of member accounts that prompts an expected total social network activity target and avoids a total expected number of complaints. The Message Diet Engine 206 aggregates each select message set permutation identified for each member account. Since each respective select message set permutation includes a minimum number of messages for a given member account that exceeds the activity target 312 and falls below the complaints threshold 318, the aggregate message set will thereby meet an expected total social network activity target for all member accounts and avoids a total expected number of complaints received from all the member accounts. The Message Diet Engine 206 sends a least a portion of the aggregate message set within the social network service to corresponding member accounts.

Figure 5:
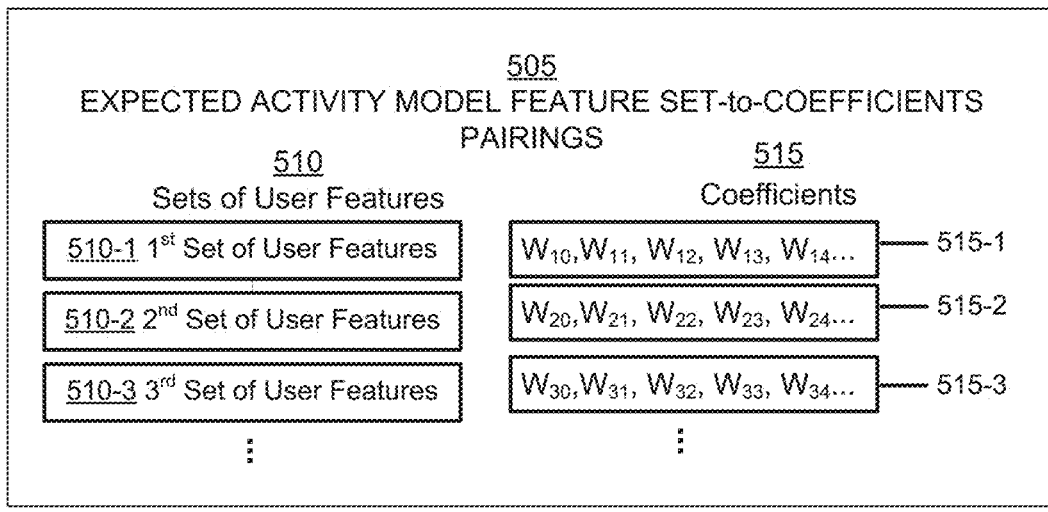
FIG. 5 is a block diagram showing example data structures of a Message Diet Engine, according to some embodiments.
Figure 5:
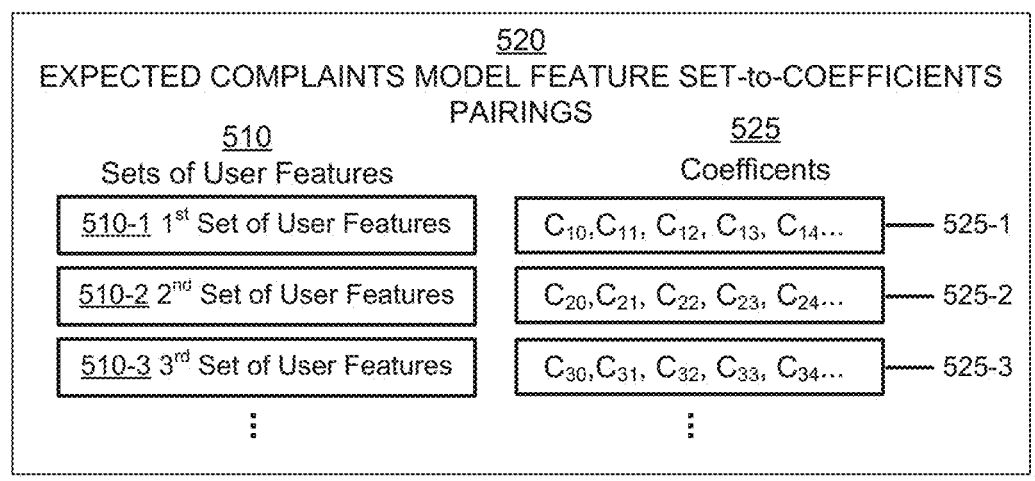

FIG. 5 is a block diagram showing example data structures of a Message Diet Engine 206, according to some embodiments.

The Message Diet Engine 206 collects historical message data. The historical message data includes a plurality of messages previously sent between various member accounts in the social network service and a respective response prompted by each previously sent message. A response can be an indication of a type of social network activity by a recipient member account in response to message receipt and can also be an indication of a complaint from the recipient member account in response to message receipt. For example, a complaint can be an unsubscribe action performed by the recipient member account and can be an identification of the previously sent message as a spam message performed by the recipient member account.

The Message Diet Engine 206 generates, based on the historical message data, an expected social network activity machine learning model 312 and an expected number of complaints machine learning model 316. The expected social network activity machine learning model 312 returns first output representing a probability that a given set of messages will prompt social network activity by a given member account. The expected number of complaints machine learning model 316 returns a number of expected number of complaints from the given member account due to receipt of a given set of messages. It is understood that a given set of messages includes various numbers of messages of one or more message types.

For the expected social network activity machine learning model 312, the Message Diet Engine 206 learns a first plurality of regression coefficients 515-1, 515-2, 515-3 . . . in order to express the probability of a target member account u being active for a first regression function in variables $n_i$ where $n_i$ is the number of emails of type i to be received by the target member account u. For example, the first regression function for the expected social network activity machine learning model 312 can be expressed as: $a_u(n_1, n_2, \ldots n_T) = w_{u0} + w_{u1} n_1 + w_{u2} n_2 + \ldots + w_{uT} n_T$. It is understood that $n_1$ represents any number of messages of a first message type and $n_2$ represents any of messages of a second message type.

Each regression coefficient in the first plurality of regression coefficients 515-1, 515-2, 515-3 . . . represents a degree of importance in which a given message type prompts social network activity by a member account having a given set of a plurality of features. As shown in FIG. 5, the expected social network activity machine learning model 312 includes a data structure for pairings 505 of sets of user features 510 to regression coefficients 515. Based on the Message Diet Engine 206 detecting the target member account has a first set of user features 510-1, a first set of coefficients 515-1 will be used in the first regression function $[a_u(n_1, n_2, \ldots n_T)=w_{u0}+w_{u1}\, n_1+w_{u2}\, n_2+ \ldots +w_{uT}\, n_T]$ by the expected social network activity machine learning model 312 to calculate a probability of target member account activity ($a_u$) if a given permutation of a set of messages is sent to the target member account. Based on the Message Diet Engine 206 detecting the target member account has a second set of user features 510-2, a second set of coefficients 515-2 will be used in the first regression function. If the Message Diet Engine 206 detects the target member account has a third set of user features 510-3, a third set of coefficients 515-3 will be used.

For the expected number of complaints machine learning model 316, the Message Diet Engine 206 learns a second plurality of regression coefficients 525-1, 525-2, 525-3 . . . . Each regression coefficient in the second plurality of regression coefficients 525-1, 525-2, 525-3 . . . represents a degree of importance in which a given message type prompts a complaint by a member account having a given set of a plurality of features. As shown in FIG. 5, the expected complaints machine learning model 316 includes a data structure for pairings 520 of sets of user features 510 to regression coefficients 525. Based on the Message Diet Engine 206 detecting the target member account has the first set of user features 510-1, a first set of coefficients 525-1 will be used in a second regression function $[c_u(n_1, n_2, \ldots n_T)=c_{u1}\, n_1+c_{u2}\, n_2+ \ldots +c_{uT}\, n_T]$ by the expected complaints machine learning model 316 to calculate an expected number of complaints ($c_u$) received from the target member account if a given permutation of a set of messages is sent to the target member account. Based on the Message Diet Engine 206 detecting the target member account has the second set of user features 510-2, a second set of coefficients 525-2 will be used in the second regression function. If the Message Diet Engine 206 detects the target member account has a third set of user features 510-3, a third set of coefficients 525-3 will be used. It is understood that a feature can be based on a type of one or more attributes, such as, for example, age (e.g., birthdate), gender, interests, contact information, home town, address, the names of the member's spouse and/or family members, educational background (e.g., schools, majors, matriculation and/or graduation dates, etc.), employment history, skills, professional organizations, social network group membership, social network discussion activity, and interactions (e.g., rating, number of views, sharing, likes) with one or more pieces of social network content.

Upon the Message Diet Engine 206 having learned the first and second regression functions using the historical message data, the Optimizer module 304 solves a multi-objective optimization problem to in order to identify a select set of messages from the message pool 302 to be sent to each respective member account.

Each message in the message pool 302 can be represented as according to a variable of e. Within the message pool 302, let $E_{ui}$ denote a given set of messages which are targeted for a given member account u that are also of type i. In addition, $z_e$ denotes a probability of sending message e. As such, an expected number of messages of type i which will be received by user u is thereby represented as, $$n_i = \sum_{e \in E_{ui}} z_e$$

According to various embodiments, the multi-objective optimization problem can hereby be represented as follows:
minimize $Z_e\, Z_e$
such that $$\sum_u \left[ w_{u0} + w_{u1} \sum_{e \in E_{u1}} z_e + w_{u2} \sum_{e \in E_{u2}} z_e + \ldots + w_{uT} \sum_{e \in E_{uT}} z_e \right]$$

> the activity target 314 and $$\sum_u \left[ c_{u1} \sum_{e \in E_{u1}} z_e + c_{u2} \sum_{e \in E_{u2}} z_e + \ldots + c_{uT} \sum_{e \in E_{uT}} z_e \right]$$

< the complaints threshold 318.

The Optimizer module 304 thereby implements the multi-objective optimization problem according to one or more encoded rules in order to calculate a solution $z_e$ for each message e.

In this manner, the disclosed Message Diet Engine 206 determines sets of messages for each member account in a plurality of member accounts that will prompt a target social network activity while avoiding receipt of an expected number of complaints.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation, and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 6:
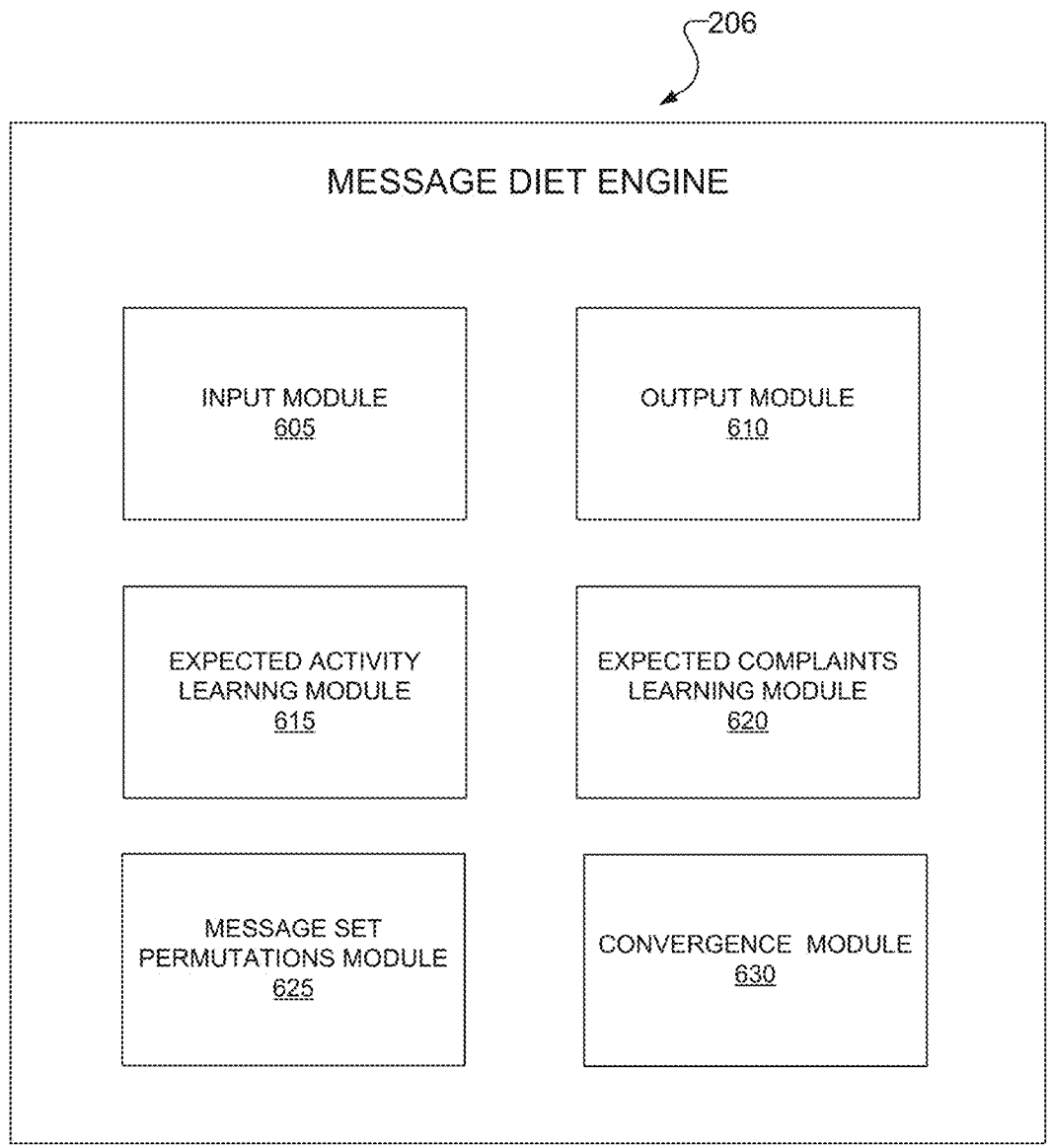
FIG. 6 is a block diagram showing example components of a Message Diet Engine, according to some embodiments.

FIG. 6 is a block diagram showing example components of a Message Diet Engine 206, according to some embodiments. It is understood that the module 605, 610, 615, 620, 625 and 630 perform one or more of the operations and actions of the various embodiments described herein. It is understood that the modules 605, 610, 615, 620, 625, 630 are included in the Message Diet Engine 206 in addition to the Optimizer module 304.

The input module 605 is a hardware-implemented module that controls, manages and stores information related to any inputs from one or more components of system 102 as illustrated in FIG. 1 and FIG. 2. In various embodiments, the inputs include at least one member account, a feature set for the at least one member account and a pool of messages where a subset of the pool of messages are generated to be targeted to the at least one member account. It is understood that member accounts can each have a different set of features.

The output module 610 is a hardware-implemented module that controls, manages and stores information related to which sends any outputs to one or more components of system 100 of FIG. 1 (e.g., one or more client devices 110, 112, third party server 130, etc.). In some embodiments, the output is a message set with a minimum amount of messages of various types for at least one member account.

The expected activity learning module 615 is a hardware implemented module which manages, controls, stores, and accesses information related to building and updating an expected social network activity machine learning model (such as the expected activity model 312). The expected activity learning module 615 also implements and executes encoded rules representing the the expected social network activity machine learning model with respect to various message set permutations.

The expected complaints learning module 620 is a hardware-implemented module which manages, controls, stores, and accesses information related to to building and updating an expected number of complaints machine learning model (such as the expected complaints model 316). The expected complaints learning module 620 also implements and executes encoded rules representing the expected number of complaints machine learning model with respect to various message set permutations.

The message set permutations module 625 is a hardware-implemented module which manages, controls, stores, and accesses information related to generating one or more message set permutations for a given member account.

The convergence module 630 is a hardware-implemented module which manages, controls, stores, and accesses information related to determining when a message set permutation has been identified that prompts an expected social network activity target and avoids an expected number of complaints.

Figure 7:
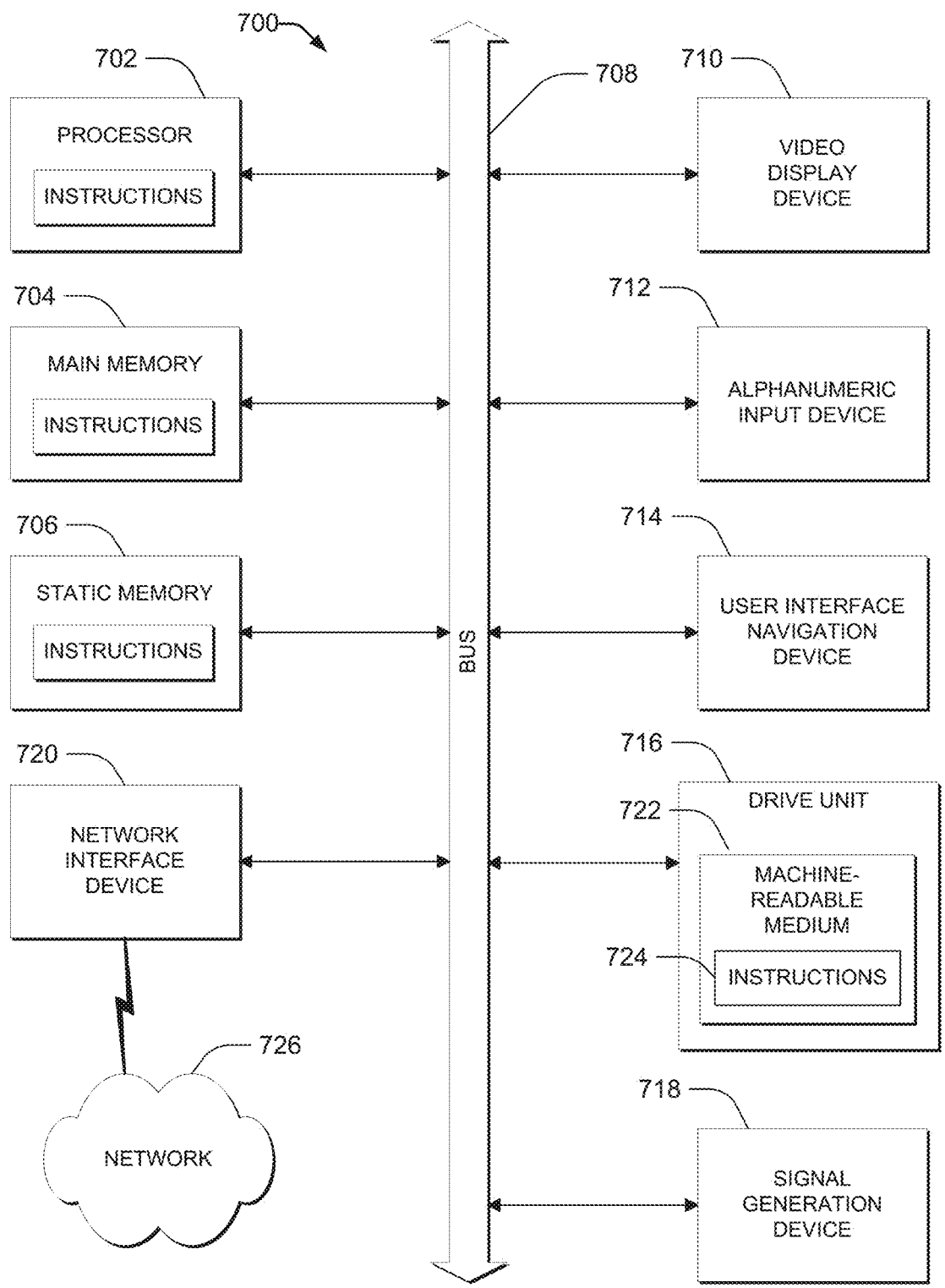
FIG. 7 is a block diagram of an example computer system on which methodologies described herein may be executed, in accordance with an example embodiment.

FIG. 7 is a block diagram of a machine in the example form of a computer system 700 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 700 includes a processor 702 (e.g., a central processing unit (CPU), a graphics processing unit (GPU) or both), a main memory 704, and a static memory 706, which communicate with each other via a bus 708. Computer system 700 may further include a video display device 710 (e.g., a liquid crystal display (LCD) or a cathode ray tube (CRT)). Computer system 700 also includes an alphanumeric input device 712 (e.g., a keyboard), a user interface (UI) navigation device 714 (e.g., a mouse or touch sensitive display), a disk drive unit 716, a signal generation device 718 (e.g., a speaker) and a network interface device 720.

Disk drive unit 716 includes a machine-readable medium 722 on which is stored one or more sets of instructions and data structures (e.g., software) 724 embodying or utilized by any one or more of the methodologies or functions described herein. Instructions 724 may also reside, completely or at least partially, within main memory 704, within static memory 706, and/or within processor 702 during execution thereof by computer system 700, main memory 704 and processor 702 also constituting machine-readable media.

While machine-readable medium 722 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present technology, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Instructions 724 may further be transmitted or received over a communications network 726 using a transmission medium. Instructions 724 may be transmitted using network interface device 720 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMAX networks). The term "transmission medium" shall be taken to include any intangible medium that is capable of storing, encoding or carrying instructions for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the technology. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer system comprising:
one or more hardware processors; and
a non-transitory machine-readable medium for storing instructions that, when executed by the one or more hardware processors, cause the one or more hardware processors to perform operations comprising:
generating a pool of messages for a plurality of member accounts of a social network service (SNS), each message being of a respective message type from a plurality of message types and targeted to a specific member account of the plurality of member accounts;
for each member account, selecting a minimum number of messages, from the pool of messages, targeted to a particular member account that prompts an expected social network activity target and avoids an expected number of complaints, the selecting of the minimum number of messages for the particular member account being based on a likely social network activity level associated with the particular member account, and based on a determined number of complaints likely to be received from a client device associated with the particular member account, a complaint including an indication of a member action associated with a message, the indication being received via a user interface of the client device associated with the particular member account;
based on the selected minimum number of messages for each member account, identifying a total minimum number of messages, from the pool of messages, to be sent to the plurality of member accounts that prompts an expected total social network activity target and avoids a total expected number of complaints; and
for each of the member accounts, causing display of one or more messages of the minimum number of messages in the user interface of the client device associated with the particular member account.

2. The computer system of claim 1, further comprising:
collecting historical message data, the historical message data comprising one or more previously sent messages in the SNS and a response prompted by the one or more previously sent messages.

3. The computer system of claim 2, wherein the response comprises at least one of an indication of social network activity by a recipient member account in response to message receipt, or an indication of a complaint from the recipient member account in response to message receipt.

4. The computer system of claim 3, wherein the complaint comprises at least one of an unsubscribe action performed by the recipient member account, or an identification of the previously sent message as a spam message performed by the recipient member account.

5. The computer system of claim 2, further comprising:
generating, based on the historical message data, an expected social network activity machine learning model and an expected number of complaints machine learning model,
wherein the expected social network activity machine learning model returns a first output representing a probability that a given set of messages of one or more message types will prompt social network activity by a given member account, and
wherein the expected number of complaints machine learning model returns a number representing an expected number of complaints from the given member account due to receipt of the given set of messages.

6. The computer system of claim 5, wherein the generating, based on the historical message data, of the expected social network activity machine learning model and of the expected number of complaints machine learning model comprises:
for the expected social network activity machine learning model:
learning a first plurality of regression coefficients, each regression coefficient in the first plurality of regression coefficients representing a degree of importance in which a given message type prompts social network activity by any member account having a given set of a plurality of features; and
for the expected number of complaints machine learning model:
learning a second plurality of regression coefficients, each regression coefficient in the second plurality of regression coefficients representing a degree of importance in which the given message type prompts a complaint by any member account having the given set of a plurality of features.

7. The computer system of claim 6, wherein the selecting of the minimum number of messages, from the pool of messages, targeted to the respective member account that prompts an expected social network activity target comprises:
identifying, via the expected social network activity machine learning model, from a first plurality of permutations of sets of messages targeted to the respective member account, a first select set of messages that meets or exceeds the expected social network activity target, the first select set of message comprising one or more message types.

8. The computer system of claim 7, wherein the selecting of the minimum number of messages, from the pool of messages, targeted to the respective member account that avoids an expected number of complaints comprises:
identifying, via the expected number of complaints machine learning model, from a second plurality of permutations of sets of messages targeted to the respective member account, a second select set of messages that avoids an expected number of complaints, the second select set of message comprising one or more message types.

9. The computer system of claim 8, further comprising:
concurrently identifying the first select set of messages with the second select set of messages.

10. The computer system of claim 9, further comprising:
identifying a select minimum number of messages to be sent to the respective member account based upon a convergence of the first select set of messages and the second select set of messages.

11. A non-transitory computer-readable medium storing executable instructions that, when executed by one or more processors, cause the one or more processors to perform operations including:
generating a pool of messages for a plurality of member accounts of a social network service (SNS), each message being of a respective message type from a plurality of message types and targeted to a specific member account of the plurality of member accounts;
for each member account, selecting a minimum number of messages, from the pool of messages, targeted to a particular member account that prompts an expected social network activity target and avoids an expected number of complaints, the selecting of the minimum number of messages for the particular member account being based on a likely social network activity level associated with the particular member account, and based on a determined number of complaints likely to be received from a client device associated with the particular member account, a complaint including an indication of a member action associated with a message, the indication being received via a user interface of the client device associated with the particular member account;

based on the selected minimum number of message for each member account, identifying a total minimum number of messages, from the pool of messages, to be sent to the plurality of member accounts that prompts an expected total social network activity target and avoids a total expected number of complaints; and for each of the member accounts, causing display of one or more messages of the minimum number of messages in the user interface of the client device associated with the particular member account.

12. The non-transitory computer-readable medium of claim 11, further comprising:

collecting historical message data, the historical message data comprising one or more previously sent messages in the SNS and a response prompted by the one or more previously sent message.

13. The non-transitory computer-readable medium of claim 12, wherein the response comprises at least one of an indication of social network activity by a recipient member account in response to message receipt, or an indication of a complaint from the recipient member account in response to message receipt.

14. The non-transitory computer-readable medium of claim 13, wherein the complaint comprises at least one of an unsubscribe action performed by the recipient member account, or an identification of the previously sent message as a spam message performed by the recipient member account.

15. The non-transitory computer-readable medium of claim 12, further comprising:

generating, based on the historical message data, an expected social network activity machine learning model and an expected number of complaints machine learning model, wherein the expected social network activity machine learning model returns a first output representing a probability that a given set of messages of one or more message types will prompt social network activity by a given member account, and wherein the expected number of complaints machine learning model returns a number representing an expected number of complaints from the given member account due to receipt of the given set of messages.

16. The non-transitory computer-readable medium of claim 15, wherein the generating, based on the historical message data, of the expected social network activity machine learning model and of the expected number of complaints machine learning model comprises:

for the expected social network activity machine learning model:

learning a first plurality of regression coefficients, each regression coefficient in the first plurality of regression coefficients representing a degree of importance in which a given message type prompts social network activity by any member account having a given set of a plurality of features; and for the expected number of complaints machine learning model:

learning a second plurality of regression coefficients, each regression coefficient in the second plurality of regression coefficients representing a degree of importance in which the given message type prompts a complaint by any member account having the given set of a plurality of features.

17. The non-transitory computer-readable medium of claim 16, wherein the selecting of the minimum number of messages, from the pool of messages, targeted to the respective member account that prompts an expected social network activity target comprises:

identifying, via the expected social network activity machine learning model, from a first plurality of permutations of sets of messages targeted to the respective member account, a first select set of messages that meets or exceeds the expected social network activity target, the first select set of message comprising one or more message types.

18. The non-transitory computer-readable medium of claim 17, wherein the selecting of the minimum number of messages, from the pool of messages, targeted to the respective member account that avoids an expected number of complaints comprises:

identifying, via the expected number of complaints machine learning model, from a second plurality of permutations of sets of messages targeted to the respective member account, a second select set of messages that avoids an expected number of complaints, the second select set of message comprising one or more message types.

19. The non-transitory computer-readable medium of claim 18, further comprising:

concurrently identifying the first select set of messages with the second select set of messages; and identifying a select minimum number of messages to be sent to the respective member account based upon a convergence of the first select set of messages and the second select set of messages.

20. A computer-implemented method, comprising:

generating, using one or more hardware processors, a pool of messages for a plurality of member accounts of a social network service (SNS), each message being of a respective message type from a plurality of message types and targeted to a specific member account of the plurality of member accounts;

for each member account, selecting a minimum number of messages, from the pool of messages, targeted to a particular member account that prompts an expected social network activity target and avoids an expected number of complaints, the selecting of the minimum number of messages for the particular member account being based on a likely social network activity level associated with the particular member account, and based on a determined number of complaints likely to be received from a client device associated with the particular member account, a complaint including an indication of a member action associated with a message, the indication being received via a user interface of the client device associated with the particular member account;

based on the selected minimum number of message for each member account, identifying a total minimum number of messages, from the pool of messages, to be sent to the plurality of member accounts that prompts an expected total social network activity target and avoids a total expected number of complaints; and for each of the member accounts, causing display of one or more messages of the minimum number of messages in the user interface of the client device associated with the particular member account.

\* \* \* \* \*